(12) United States Patent
Zellhuber et al.

(10) Patent No.: US 10,975,015 B2
(45) Date of Patent: Apr. 13, 2021

(54) PROCESS AND PLANT FOR PRODUCING ETHYLENE AND ACETIC ACID

(71) Applicant: LINDE AKTIENGESELLSCHAFT, Munich (DE)

(72) Inventors: Mathieu Zellhuber, Martinsried (DE); Florian Winkler, Munich (DE); Martin Schubert, Munich (DE); Andreas Meiswinkel, Rimsting (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 16/472,473

(22) PCT Filed: Dec. 22, 2017

(86) PCT No.: PCT/EP2017/084338
§ 371 (c)(1),
(2) Date: Jun. 21, 2019

(87) PCT Pub. No.: WO2018/115416
PCT Pub. Date: Jun. 28, 2018

(65) Prior Publication Data
US 2020/0239396 A1 Jul. 30, 2020

(30) Foreign Application Priority Data

Dec. 22, 2016 (EP) .................................... 16206435

(51) Int. Cl.
*C07C 51/215* (2006.01)
*C07C 5/48* (2006.01)
(Continued)

(52) U.S. Cl.
CPC .............. *C07C 51/215* (2013.01); *C07C 5/48* (2013.01); *C07C 11/04* (2013.01); *C07C 53/08* (2013.01)

(58) Field of Classification Search
None
See application file for complete search history.

(56) References Cited

U.S. PATENT DOCUMENTS 4,899,003 A 2/1990 Manyik et al.

FOREIGN PATENT DOCUMENTS

EP 1201630 A2 5/2002

OTHER PUBLICATIONS

Cavani ("Oxidative dehydrogenation of ethane and propane: How far from commercial implementation?" Catalysis Today 127, 2007, p. 113-131) (Year: 2007).*

(Continued)

*Primary Examiner* — Amy C Bonaparte
(74) *Attorney, Agent, or Firm* — Lathrop GPM LLP (57) ABSTRACT

A process for producing ethylene and acetic acid is proposed in which an ethane- and oxygen-containing reaction input stream is formed and a portion of the ethane and of the oxygen in the reaction input stream is converted into the ethylene and the acetic acid by oxidative dehydrogenation to obtain a process gas, wherein the process gas contains the unconverted portion of the ethane and of the oxygen, the ethylene and the acetic acid and also water. It is provided that the process comprises adjusting in the process gas a water partial pressure according to a specified product ratio of the acetic acid to the ethylene to a value in a range between 0.7 and 5 bar (abs.). A corresponding plant (100) likewise forms part of the subject matter of the present invention.

10 Claims, 4 Drawing Sheets

(51) Int. Cl.
 *C07C 11/04* (2006.01)
 *C07C 53/08* (2006.01)

(56) References Cited

OTHER PUBLICATIONS

Gartner ("Oxidative Dehydrogenation of Ethane: Common Principles and Mechanistic Aspects" ChemCatChem 2013, 5, p. 3196-3217) (Year: 2013).*
PCT/EP2017/084338 English translation of International Search Report dated Mar. 20, 2018, 2 pages.
PCT/EP2017/084338 English translation of International Preliminary Report on Patentability Chapter II dated Jun. 27, 2019, 6 pages.

* cited by examiner

PROCESS AND PLANT FOR PRODUCING ETHYLENE AND ACETIC ACID

The invention relates to a process for producing ethylene and acetic acid and to a corresponding plant according to the preamble of the independent claims.

PRIOR ART

Oxidative dehydrogenation (ODH) of paraffins having two to four carbon atoms is known in principle. In ODH the recited paraffins are reacted with oxygen to afford inter alia the respective olefins and water.

ODH may be advantageous compared to established processes for producing olefins such as steamcracking or catalytic dehydrogenation. For instance, there is no thermodynamic equilibrium limitation on account of the exothermicity of the reactions involved. ODH may be performed at comparatively low reaction temperatures. Regeneration of the employed catalysts is in principle not necessary since the presence of oxygen allows an in situ regeneration. Finally, compared to steamcracking, smaller amounts of worthless byproducts such as coke are formed.

For further details concerning ODH, reference is made to the relevant technical literature, for example Ivars, F. and López Nieto, J. M., Light Alkanes Oxidation: Targets Reached and Current Challenges, in: Duprez, D. and Cavani, F. (ed.), Handbook of Advanced Methods and Processes in Oxidation Catalysis: From Laboratory to Industry, London 2014: Imperial College Press, pages 767-834, or Gärtner, C. A. et al., Oxidative Dehydrogenation of Ethane: Common Principles and Mechanistic Aspects, Chem Cat Chem, vol. 5, no. 11, 2013, pages 3196 to 3217.

Particularly when using MoVNbTeOx catalysts under industrially relevant reaction conditions ODH forms significant amounts of the respective carboxylic acids of the employed paraffins as by-products. For economic plant operation corresponding coproduction of olefins and the respective carboxylic acids is generally necessary when using the described catalyst type. This applies in particular to the production of ethylene by ODH of ethene (ODH-E) which simultaneously forms acetic acid.

In industrial practice coproduction processes are regarded as of less interest since they always entail limited production flexibility. In order to make such a process attractive the operator must be provided with an easily controllable, flexible plant in order to permit the simplest possible adaptation of the product distribution to the actual and/or economically useful requirements. The present invention has this for its object.

DISCLOSURE OF THE INVENTION

Against this background, the present invention proposes a process for producing ethylene and acetic acid and a corresponding plant having the features of the independent claims. Embodiments are in each case subject matter of the dependent claims and of the description which follows.

Material streams, gas mixtures etc. may in the context of the present usage of the terms be rich or poor in one or more components, wherein the indication "rich" may represent a content of not less than 95%, 96%, 97%, 98%, 99%, 99.5%, 99.9% or 99.99% and the indication "poor" may represent a content of not more than 5%, 4%, 3%, 2%, 1%, 0.5%, 0.1% or 0.01% on a molar, weight or volume basis. If a plurality of components are reported the indication "rich" or "poor" relates to the sum of all components. If reference is made for example to "oxygen" or "ethane" a pure gas or else a mixture rich in the respective component may be concerned.

The terms "pressure level" and "temperature level" are used hereinbelow to characterize pressures and temperatures, these being intended to express that pressures and temperatures need not be used in the form of exact pressure/temperature values. A pressure level or temperature level may for example be within ±1%, 5%, 10%, 20% or 50% of a mean value. A plurality of pressure and temperature levels may represent disjoint or overlapping ranges. The same pressure/temperature level may for example still be present even when pressures and temperatures have been reduced on account of transmission losses or cooling. Pressure levels reported here in bar are absolute pressures.

A "rectification column" is in the context of the present usage of the term a separating unit adapted for at least partly fractionating a substance mixture introduced in gaseous or liquid form or in the form of a biphasic mixture having liquid and gaseous proportions, optionally also in the supercritical state, by rectification, i.e. respectively generating from the substance mixture pure substances or at least substance mixtures having different compositions. Rectification columns are typically configured as cylindrical metal containers provided with internals, for example separating trays or ordered or unordered packings. A rectification column comprises a bottoms evaporator. This is a device having a heat exchanger which is heated and which is adapted for heating a liquid fraction accumulating in the bottom of the rectification column, also known as bottoms liquid. By means of a bottoms evaporator a portion of the bottoms product is continuously evaporated and recycled in gaseous form into the separating region.

Advantages of the Invention

As mentioned, for economic plant operation coproduction of ethylene and acetic acid is generally necessary when using the described catalyst type in ODH-E although in industrial practice coproduction processes are regarded as less attractive. The configuration of a flexible catalytic process is challenging, in particular when an exothermic process such as ODH-E is concerned. In this case the danger of thermal runaway must always be prevented which severely limits adjustment of some of the operating parameters. The catalytic processes further include a multiplicity of partial reactions which exert reciprocal influence on one another. It is therefore generally very difficult to identify suitable process variables which reliably describe the reaction and are suitable as a process control variable.

If reference is made hereinbelow to a production of ethylene and acetic acid this does not exclude the additional formation of higher olefins and carboxylic acids in the context of the process according to the invention, in particular when using corresponding feeds containing higher paraffins. While steamcracking, for example, can also form lighter olefins from heavier paraffins, for example ethylene from propane, this is typically not the case in ODH, in particular ODH-E. Accordingly, propane is here predominantly converted into propylene and acrylic acid (propenoic acid) but not into ethylene. The carboxylic acids formed in ODH are typically removed with water from a process gas stream formed in ODH. When paraffins of different chain lengths are employed, an aqueous solution of different carboxylic acids is obtained. If this, and the simultaneous formation of higher olefins, is not desired, a reaction input stream may be formed so as to contain no higher paraffins, for example by a removal provided upstream.

The present invention is based on the surprising finding that at a water partial pressure at the outlet of one or more reactors used for ODH-E in the range from 0.5 to 5 bar (abs.), in particular of 0.7 to 3 bar (abs.), the molar flow ratio of acetic acid to ethylene in the outlet stream (predominantly referred to hereinbelow as "process gas") varies almost linearly with the water partial pressure at the outlet. This value may therefore be used as a process control variable when a particular product ratio of acetic acid to ethylene is to be established. The water partial pressure in the process gas is the result not only of the water addition at the reactor inlet and in a corresponding reaction input stream but also of the conversion of the ethane in the reactor and thus potentially also of the instantaneous catalyst activity. In contrast to an adjustment merely of the water content in the reaction input stream which without knowledge of the recited further influencing variables may result in greatly varying water partial pressures in the process gas and thus varying product ratios, the use of the water partial pressure in the process gas as a process control variable can therefore achieve a very much more exact establishment of the desired product ratio.

An adjustment of the water content in the reaction input stream, but not in the process gas, is described in EP 1 201 630 A2. Furthermore, it is also reported here that pressure, temperature and residence time in the reaction zone may be controlled. However, the magnitude of the water content in the process gas is not addressed here. The same also applies for a process described in U.S. Pat. No. 4,899,003 A. There is therefore a lack in both cases of the finding according to the invention that the water partial pressure at the reactor outlet constitutes a process control variable by means of which the product selectivity of a process in which a coproduction of ethylene and acetic acid by ODH-E using the mentioned catalyst type is undertaken may be particularly reliably adjusted.

The recited physical laws according to the invention were initially determined in the context of ethane oxidation experimental series with constant inlet temperature and varying water content in the reaction input stream using a MoVNbTeOx catalyst. A virtually constant conversion of the ethane was achieved at likewise virtually constant selectivity for carbon dioxide and carbon monoxide. By contrast, the molar amounts of the desired products ethylene and acetic acid developed conversely to one another in precisely this region. In the recited region a constant, nearly linear contrary profile of the product molar flow ratio of acetic acid to ethylene is observed. For further elucidation reference is made to the attached FIGS. 2 and 3 and the accompanying elucidations.

In addition analogous experimental series were performed at different flow rates and thus different space velocities (weight hourly space velocity, WHSV) and temperatures in the reactor. At a higher flow rate and thus higher space velocity and lower temperature, lower conversion rates are observed as expected but the ratio of the two product molar flows at identical water partial pressures at the reactor outlet is virtually identical to the values determined at a lower flow rate. This shows that in the recited region the process control may be based decisively on the water partial pressure at the outlet. The partly clearly linear profile of the product molar flow ratio becomes apparent especially for economically relevant operation at higher conversions.

Further experimental series were performed using a test reactor and the abovementioned relationships were likewise verified. Reference is made in particular to the attached FIG. 6 and the accompanying elucidations for details.

The present invention therefore proposes a process for producing ethylene and acetic acid in which an ethane- and oxygen-containing reaction input stream is formed and a portion of the ethane and of the oxygen in the reaction input stream is converted into the ethylene and the acetic acid by oxidative dehydrogenation to obtain a process gas, wherein the process gas contains the unconverted portion of the ethane and of the oxygen, the ethylene and the acetic acid and also water. As mentioned, such a process gas also contains further byproducts such as carbon monoxide and carbon dioxide. According to the invention it is provided that in the process gas a water partial pressure is adjusted according to a specified product ratio, in particular a specified product molar flow ratio, of the acetic acid to the ethylene to a value in a range between 0.5 to 5 bar (abs.), in particular in a range between 0.7 and 3 bar (abs.). As mentioned, an unchangingly constant, virtually linear product molar flow ratio of acetic acid to ethylene is achieved in the range for different conversions and operating conditions so that a particularly readily controllable coproduction of these compounds with adjustable production emphasis is possible here.

A "reaction input stream" is in the context of the present usage of the term the entire gas mixture subjected to ODH. This may in particular also be supplied to the reactor(s) used in the form of separate material streams. For example a paraffin-containing material stream and an oxygen-containing material stream may be combined to afford a corresponding reaction input stream in the reactor(s) used or upstream of the reactor(s).

A "forming" of the reaction input stream may comprise any process engineering treatment such as compression, decompression, cooling or heating, or else removing of substreams, supplying of further material streams or a chemical reaction of components. In the context of the present invention the forming of the reaction input stream in particular comprises for example heating a material stream that is converted into the reaction input stream. In this heating, the so-called feed preheating, the reaction input stream may be brought to a temperature which allows startup of the ODH in a downstream reaction unit having one or more reactors.

In particular it may be provided in a process according to an embodiment of the invention that the forming of the reaction input stream comprises combining a material stream with one or more further fluids. In this way suitable media which for example have a favorable influence on the reaction conditions in the ODH may be supplied. As mentioned, ODH is a strongly exothermic reaction and so-called diluents such as inert gases or steam are therefore typically added to prevent thermal runaway. Such diluents may be added during formation of the reaction input stream or else only in one or more reactors, as desired. It is also possible for example to add oxygen or an oxygen-containing gas mixture required in the ODH already during formation of the reaction input stream. This may also only be effected later.

In the context of the present invention it is advantageous when the water partial pressure is measured and a control means is used by which the water partial pressure is adjusted using at least one manipulated variable. As mentioned, a control means based on the water partial pressure can achieve a much more precise adjustment of the product ratio than when merely a water addition in the reaction input stream were to be controlled.

As mentioned, the present invention is employed in particular when in the oxidative dehydrogenation a catalyst containing at least the elements molybdenum, vanadium, niobium and optionally tellurium, i.e. a so-called MoVTeNbO catalyst, is used because, upon use of such a catalyst, ethylene and acetic acid are formed and the mentioned physical laws are established.

In the context of the present invention the oxidative dehydrogenation is advantageously performed with an ethane conversion of at least 15%. The ethane conversion may in particular be at least 20, 25, 30, 35, 40 or 45%. The ethane conversion is in particular below 75%. The specified product molar flow ratio of acetic acid to ethylene is in particular in a range from 0.05 to 0.5.

The term "conversion" is to be understood here as meaning the molar proportion of employed reactants, here ethane, which altogether reacts to afford primary products and byproducts. The "product molar flow" of a component describes the molar amount of a component which exits one or more reactors per unit time.

The water partial pressure in the process gas may in the context of the present invention be adjusted in particular by addition of water to the reaction input stream and/or by adjustment of a reactor temperature at which the oxidative dehydrogenation is performed. These are thus suitable manipulated variables for the mentioned control means. It may for example also be provided for to undertake a course adjustment by means of a water addition to the reaction input stream and a fine adjustment by adjustment of a reactor temperature. A higher reaction temperature results in a higher conversion and thus a higher formation of water of reaction. Thus the water partial pressure in the process gas is at least partly adjusted by adjustment of the reactor temperature. The added amount of oxygen in the reaction input stream proves a further decisive influencing variable. In the context of the present invention this parameter is always adapted such that at the reactor outlet an oxygen content in the process gas between 0.01 mol % and 50 mol %, preferably between 0.1 and 5 mol %, particularly preferably between 0.1 and 0.5 mol %, is always satisfied to prevent a reduction of the catalyst material through lack of oxygen and also to limit safety engineering risks due to high oxygen contents. However, it is as a result of these limitations that the control means for the oxygen metering is downstream of the fundamental setting of the operating point and has no appreciable influence on the product molar flow ratio provided that it is ensured that the abovementioned range for the oxygen content in the outlet is satisfied.

According to the present invention the water partial pressure to be adjusted is to be understood as meaning the partial pressure at the reactor outlet of one or more reactors used for the oxidative dehydrogenation, for example immediately downstream of a catalyst bed or a conduit connected therewith. In particular a process gas from the oxidative dehydrogenation has not yet been subjected to any measures that change its composition, in particular a cooling, a scrub and like, at the reactor outlet.

It is particularly advantageous when the water partial pressure is captured at the reactor outlet of the reactor(s). Methods for water determination and thus for determining the water partial pressure are known in principles to those skilled in the art. Commonly used absorption spectroscopy methods, for example Fourier-transformed infrared spectroscopy (FTIR) or tunable diode laser absorption spectroscopy (TDLAS), in combination with commonly used methods of pressure measurement may be concerned here, for example.

It is particularly advantageous when the oxidative dehydration is performed in the context of the present invention in a temperature range of 240° C. to 500° C. in a reactor bed of the reactor(s) used. In particular the temperature range may be 260° C. and 400° C., particularly preferably 280° C. to 350° C. The total pressure at the reactor inlet of the reactor(s) is preferably between 1 and 10 bar (abs.), in particular between 2 and 9 bar (abs.), more particularly between 3 and 8 bar (abs.). The space velocity in the reactor bed of the reactor(s) (WHSV) is in the range between 0.1 and 10 kg of ethane/(h×kg of catalyst), preferably between 0.5 and 5 kg of ethane/(h×kg of catalyst), particularly preferably between 0.7 and 3 kg of ethane/(h×kg of catalyst). The previously elucidated adjustability of the product molar flows is possible in this range in particular.

The process according to the invention may in particular be performed using one or more diluents that are added to the reaction input stream and pass into the process gas. The use of such diluents, which in particular ensure that during the strongly exothermic ODH a stable and safe reactor operation is guaranteed, is known in principle. As mentioned, to adjust the desired water partial pressure in the recited range in particular an addition of water/water vapor into the reaction input stream may be effected. This water/this water vapor simultaneously acts as diluent. However, alternatively or in addition one or more further diluents may be used.

In particular, in the context of the present invention one or more diluents selected from the group consisting of water, methane, nitrogen and at least one further inert gas may be used. Carbon dioxide too may be used as diluent. Only a small proportion, if any, of such diluents take part in the reaction in the reactor(s) and therefore at least the predominant portion passes into the process gas.

In the context of the present invention it has further been found that even in case of introduction of ethylene as an additional feed stream into the reactor, i.e. as part of the reaction input stream, there is a strong functional relationship between the product molar flow ratio of ethylene and acetic acid and the water partial pressure at the reactor outlet. The described plant operating mode can accordingly also be applied in the case of additional ethylene introduction. This makes it possible for example to further intensify the flexibility towards more acetic acid as product, albeit then with expected higher losses to carbon monoxide and carbon dioxide. In certain cases a process variant in which ethylene is further added to the reaction input stream in a specified amount, in particular from 0 to 50 mol %, may thus be advantageous.

The introduction of additional ethylene may be effected either in the form of an introduction from an external source or else in the form of a recycling of a corresponding fraction from the separation part of the plant. The "separation part" is an arrangement in which by thermal separation components or component groups are removed from the process gas or from a gas mixture obtained therefrom. This recycling may be effected by additional removal of a corresponding fraction in the separation part or by changing the bottoms product specification in a rectification column used for separating ethane and ethylene provided in the separation part. In this case, by adaptation of the separating conditions such as tops temperature or pressure or else by use of a correspondingly configured "lower resolution" separating rectification column, a portion of the product ethylene otherwise withdrawn as a tops product is specifically transferred into the bottom of the rectification column and withdrawn there in an otherwise predominantly ethane-containing fraction. Said fraction may be recycled into the reactor(s).

The present invention further extends to a plant for producing ethylene and acetic acid which is adapted for forming an ethane- and oxygen-containing reaction input stream and converting a portion of the ethane and of the oxygen in the reaction input stream into the ethylene and the acetic acid by oxidative dehydrogenation to obtain a process gas, wherein the process gas contains the unconverted portion of the ethane and of the oxygen, the ethylene and the acetic acid and also water. According to the invention it is provided that the plant comprises means adapted for adjusting in the process gas a water partial pressure according to a specified product ratio of the acetic acid to the ethylene to a value in a range between 0.5 and 5 bar (abs.), in particular in a range between 0.7 and 3 bar (abs.).

For features and advantages of a corresponding plant, reference is made to the above elucidations concerning the features and advantages of the process. In particular such a plant is adapted for performing a process according to the specific embodiments elucidated above and comprises means suitable therefor. In this regard too reference is made to the above intimations.

The invention is more particularly elucidated below with reference to the appended drawings which illustrate inter alia preferred embodiments of the present invention.

DETAILED DESCRIPTION OF THE DRAWINGS

In the figures that follow functionally or structurally equivalent elements are indicated with identical reference numerals and for the sake of simplicity are not repeatedly elucidated. When plant parts are described hereinbelow the elucidations concerning these also apply correspondingly to the process steps implemented by means of these plant parts and vice versa.

Figure 1:
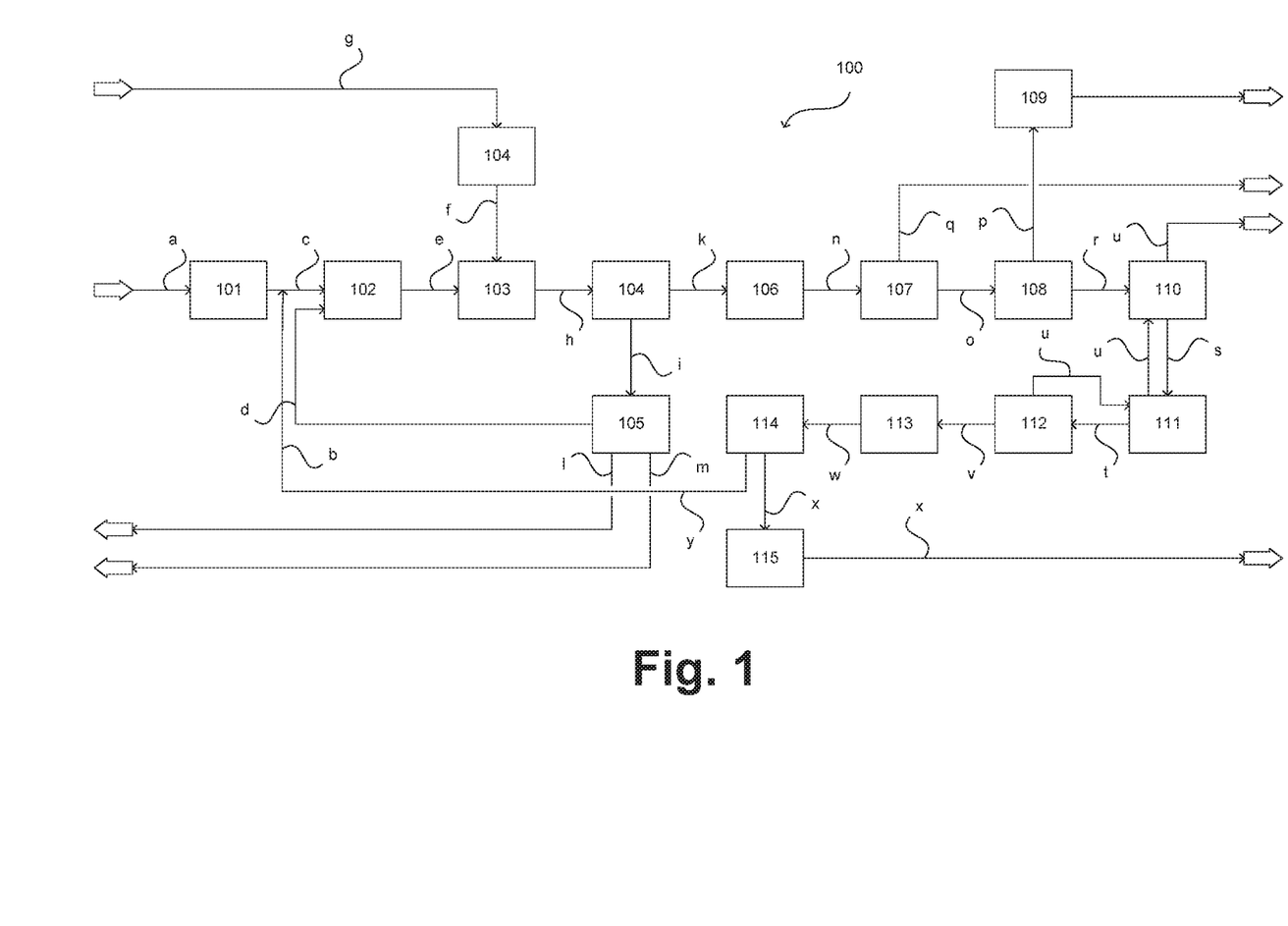
FIG. 1 shows a plant for producing ethylene and acetic acid according to one embodiment of the invention.

In FIG. 1 a plant for producing olefins according to one embodiment of the invention in the form of a greatly simplified plant diagram is illustrated and collectively referred to as 100. Notwithstanding that a plant 100 for ODH of ethane (ODH-E) is described below, the present invention is also suitable, as recited, for use in ODH of higher hydrocarbons. In this case the elucidations which follow apply correspondingly.

In the plant 100 a separation input in the form of a material stream a is supplied to a rectification unit 101 having for example one or more rectification columns and subjected to a rectification. In the depicted example the separation input contains at least ethane and higher hydrocarbons, in particular corresponding higher paraffins. The rectification unit 101 may also be supplied with one or more further separation inputs, for example the material stream b shown here and more particularly elucidated below.

In the rectification unit 101 the separation input is subjected to a rectification alone or together with the further separation input(s) to obtain a gas mixture which contains ethane but is poor in higher hydrocarbons. The gas mixture is withdrawn in the form of a material stream c and supplied to a preheating unit 102. In the preheating unit 102 the gas mixture is preheated, wherein in the depicted example the preheating unit 102 is also supplied with a water or steam stream d. Further material streams may also be supplied, as is illustrated here in the form of a material stream b. Further obtained in the rectification unit 101 is a component mixture containing predominantly or exclusively the higher hydrocarbons. Said mixture is not shown explicitly.

A material stream e outflowing from the preheating unit 102 is supplied to a reaction unit 103 to form a reaction input stream. On account of its formation using the separated product from the rectification unit 101 the reaction input stream contains ethane but is poor in higher hydrocarbons. The reaction input stream may further contain one or more diluents such as water or inert gases and further components. These may also be supplied to the reaction unit 103 in the form of further material streams (not shown).

In the depicted example the reaction unit 103 is supplied with an oxygen-containing material stream f. This may be provided using an air separation plant 104. To this end the air separation plant 104 is supplied with an airstream g. The oxygen-containing material stream f may be substantially pure oxygen but fractions of nitrogen and of noble gases may also be present depending on the operation of the air separation plant 104. In this way it is likewise possible to supply diluent.

Outflowing from the reaction unit 103 is a process gas in the form of a process gas stream h which contains ethylene formed in the reaction unit 103 by ODH of a portion of the ethane in the reaction input stream. The product mixture further contains acetic acid likewise formed from ethane during ODH in the reaction unit 103, water, carbon monoxide, carbon dioxide, unconverted oxygen and the diluent(s) and further compounds if added or previously formed in the reaction unit 103.

It will be appreciated that reaction unit 103 may comprise a or else a plurality of reactors which are for example operated in parallel. In the latter case these reactors are each supplied with corresponding reaction inputs, which may have identical or different compositions, and corresponding oxygen-containing material streams f and in each case corresponding process gas streams h are formed. The latter may for example be combined and supplied together as process gas to the units elucidated below.

Downstream of the reaction unit 103 a water partial pressure may be captured. This may be adjusted for example by an addition of water/steam in the form of the material stream d into the preheating unit 102. A further influencing, in particular a fine adjustment, may be effected by adjustment of the temperature in the reaction unit 103.

The process gas is transferred into a quench unit 104 in which, for example in a quench column, it may be contacted with quench water or a suitable aqueous solution. In the quench unit 104 the process gas is in particular cooled and the acetic acid formed in the reaction unit 103 is scrubbed out of the process gas. Acetic acid-laden process water outflows from the quench unit 104 in the form of a material stream i, the process gas at least largely freed of acetic acid outflows from the quench unit 104 in the form of a material stream k.

In an optional acetic acid recovery unit 105 acetic acid is separated off from the acetic acid-laden process water as glacial acetic acid which is discharged from the plant 100 as material stream l. Pure process water likewise recovered in the acetic acid recovery unit 105 may be supplied to the preheating unit 102 in the form of the previously elucidated material stream d. The process water supplied to the reactor may also be provided partly or fully in the form of externally supplied freshwater. Water that is no longer usable or required may be discharged from the plant 100 and supplied to a wastewater treatment in the form of a wastewater stream m.

The process gas present in the form of material stream k and at least largely freed of acetic acid is compressed to a suitable pressure level, for example 15 to 25 bar, in a compressing unit 106 and in the form of a compressed material stream n supplied to an amine scrub unit 107. Scrubbed out therein are in particular portions of the carbon dioxide present in the process gas. After regeneration of the amine the scrubbed-out carbon dioxide may be discharged from the plant in the form of a material stream q. The process gas thus partly freed of carbon dioxide is transferred in the form of a material stream o into a lye scrub unit 108 and further purified of carbon dioxide therein. Generated in the lye scrub unit 108 is waste lye which in the form of a material stream p may be transferred into a waste lye treatment unit 109 and finally discharged from the plant 100.

The process gas further purified in the lye scrub unit 108 is transferred in the form of a material stream r into a pre-cooling and drying unit 110 where it may be freed from residual water in particular. The dried process gas is transferred in the form of a material stream s into a low temperature unit 111 and subsequently in further-cooled form in the form of one or more material streams t into a demethanization unit 112. In the low temperature unit 111 and the demethanization unit 112 components lower boiling than ethylene, in particular carbon monoxide and oxygen, are separated off from the process gas, wherein the remainder stays in condensed form. If the process gas contains higher hydrocarbons formed as a byproduct during ODH in the reaction unit 103 these are likewise converted into the condensate.

The separated-off components lower boiling than ethylene are recycled in the form of one or more material streams u through the low temperature unit 111 and the precooling and drying unit 110, therein optionally combined with further corresponding material streams, used for cooling purposes and discharged from the plant 100. If required the hydrocarbons having two and optionally more carbon atoms are supplied in the form of a material stream v to a hydrogenation unit 113 in which in particular acetylene likewise formed as byproduct during ODH in the reaction unit 103 may be hydrogenated. After the hydrogenation the material stream now referred to as w is transferred into an ethylene removal unit 114.

In the ethylene removal unit 114 ethylene is at least largely separated off from other components and in the form of a material stream x after utilization in an ethylene cooling unit 115 may be discharged from the plant 100 in gaseous form. The remaining components, predominantly ethane and optionally higher hydrocarbons, are withdrawn in the form of a material stream y. If higher hydrocarbons are present therein these are advantageously recycled into the reaction unit in the form of the previously recited material stream b. An optional workup of this material stream b may be effected.

Through an adapted operation of the ethylene removal unit 114/a corresponding configuration, a portion of the ethylene may also be passed into material stream y/b and recycled into the process therein. It is also possible to recycle the material stream x or a portion thereof. In this way the yield of acetic acid may, as mentioned, be increased when required. It is expressly emphasized that in the context of the present invention certain plant parts, in particular for example the rectification unit 101, may be eschewed. In this case the material stream y may for example also be introduced directly into the preheating unit 102 or into the reaction unit 103. Further variants are possible and encompassed by the present invention.

Figure 2:
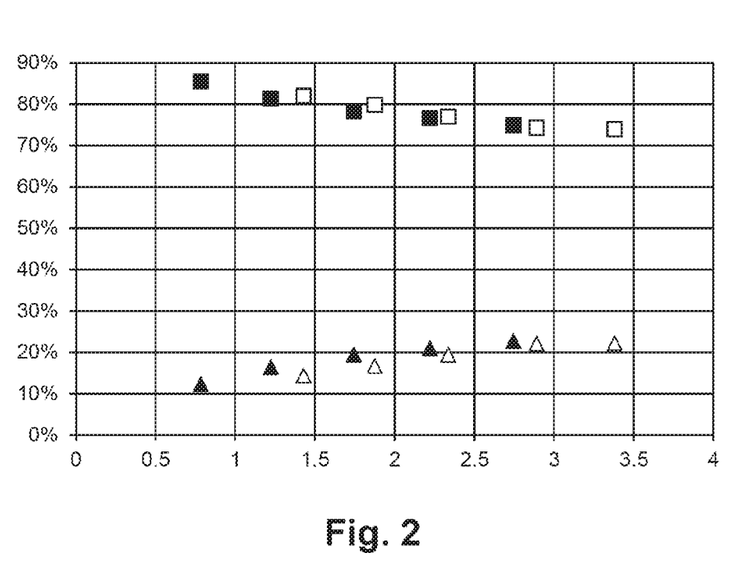
FIG. 2 shows selectivities for ethylene and acetic acid obtained in a process according to one embodiment of the invention.

FIG. 2 shows selectivities for ethylene and acetic acid obtained in a process according to one embodiment of the invention in a diagram in which water partial pressures in bar (abs.) are plotted on the abscissa against selectivity values in percent on the ordinate. The selectivity values for the individual products shown are calculated from the ratio of the respective product molar flow based on the molar amount of ethane converted in the reactor per unit time.

The data shown relate to two experimental series with different flow rates, thus different space velocities and different temperatures. No ethylene was added at the reactor inlet in either experimental series. Higher flow rates give rise to lower conversions as expected (about 19% compared to about 40%) but the product selectivities and thus the product molar flow ratio (corresponds here to the ratio of both selectivities) at identical water partial pressures at the reactor outlet are virtually identical. This shows that in the recited region the process control may be based decisively on the water partial pressure at the outlet.

The values obtained at the higher flow rates and lower conversion rates are shown for ethylene with shaded (black) squares and for acetic acid with shaded (black) triangles, the values obtained at the lower flow rates and higher conversion rates are correspondingly shown for ethylene with unshaded (white) squares and for acetic acid with unshaded (white) triangles.

Figure 3:
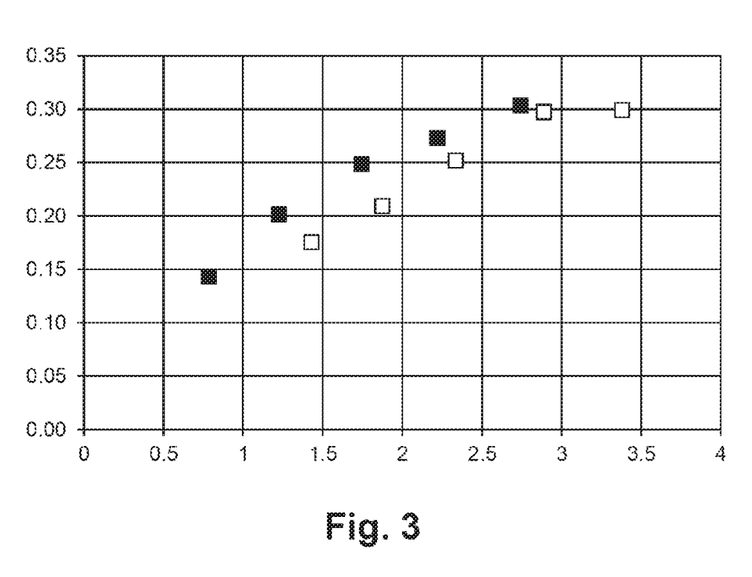
FIG. 3 shows product molar flow ratios in respect of ethylene and acetic acid obtained in a process according to one embodiment of the invention.

The ratio of the product amounts as a function of the water partial pressure at the reactor outlet is shown again in FIG. 3. Here, the water partial pressures in bar (abs.) are plotted on the abscissa against the product molar flow ratio of acetic acid to ethylene (corresponds here to the ratio of the values shown in FIG. 2 to one another). Here, the product molar flow ratios for the higher flow rates and lower conversion rates are shown with shaded (black) squares and for the lower flow rates and higher conversion rates are shown with unshaded (white) squares. The partly clearly linear profile of the product mix becomes apparent especially for economically relevant operation at higher conversions.

This simplified behavior of the reaction system may be explained by two effects confirmed by experiment but declared here explicitly as nonbinding: At elevated water partial pressures the oxidation of formed ethylene is promoted and the selectivity for formation of acetic acid increases. Simultaneously, the desorption of the formed acetic acid from the catalyst surface is promoted by elevated water partial pressures, as a result of which less acetic acid is available for the subsequent oxidation of acetic acid to carbon monoxide and carbon dioxide which likewise takes place at the catalyst. This results in the shifting of the overall selectivity toward acetic acid while selectivity for carbon monoxide and carbon dioxide remains virtually unchanged.

Figure 4:
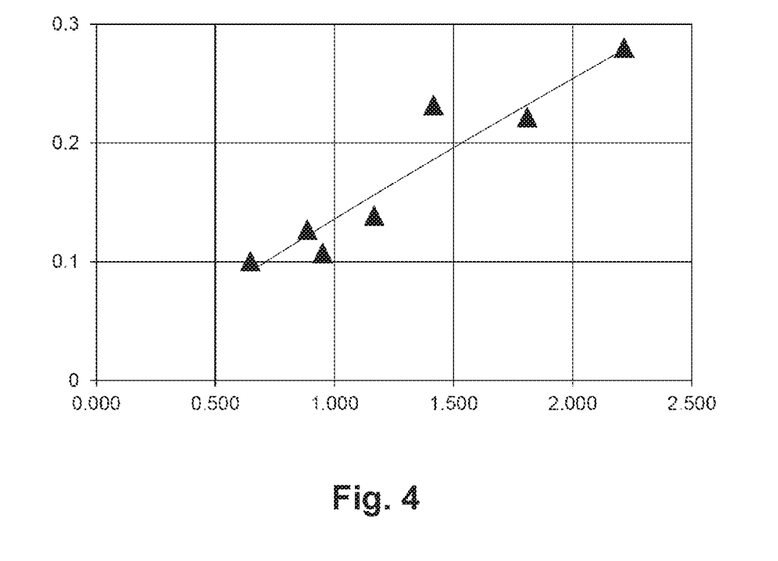
FIG. 4 shows product molar flow ratios in respect of ethylene and acetic acid obtained in a process according to one embodiment of the invention.

The determining influence of the water partial pressure at the outlet on the product ratio between acetic acid and ethylene may be verified by further measurements, partly using different dilution media and greatly varying experimental conditions. In this regard reference is made to FIG. 4 which shows corresponding product molar flow ratios of acetic acid to ethylene. The representation corresponds to that of FIG. 3.

Figure 5:
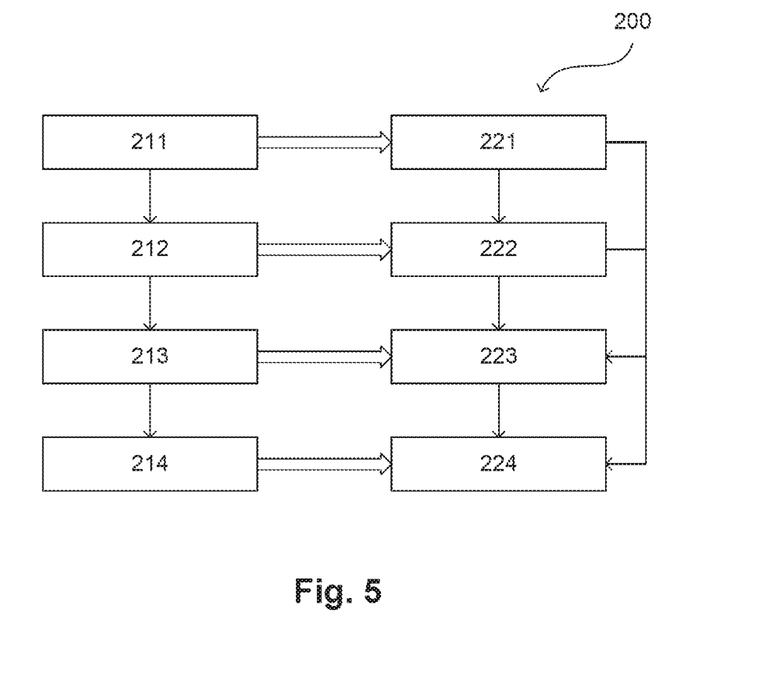
FIG. 5 shows a plant according to one embodiment of the invention.

FIG. 5 shows a process according to one embodiment of the invention in the form of a schematic flow plan given the collective label 200. 211 to 214 denote partial goals to be achieved and 221 to 224 denote the specific adjustments/specifications to be undertaken therefor.

The desired product distribution of acetic acid to ethylene is specified in step 211. On this basis in step 221 a target value for the water partial pressure at the reactor outlet is set. On the basis of a total product amount specified in step 212 and accompanying recycle amounts, in step 222 a flow rate and thus the conversion in the reactor (see in particular FIGS. 2 and 3 in this regard) is set.

In step 213 a correspondingly defined operating point is established to which end in step 223 a water content in the reaction input stream is adjusted. The fine adjustment of the operating point, step 214, is effected by an adapting of the reactor temperature in step 224. In each case the water partial pressure at the reactor outlet is monitored.

Figure 6:
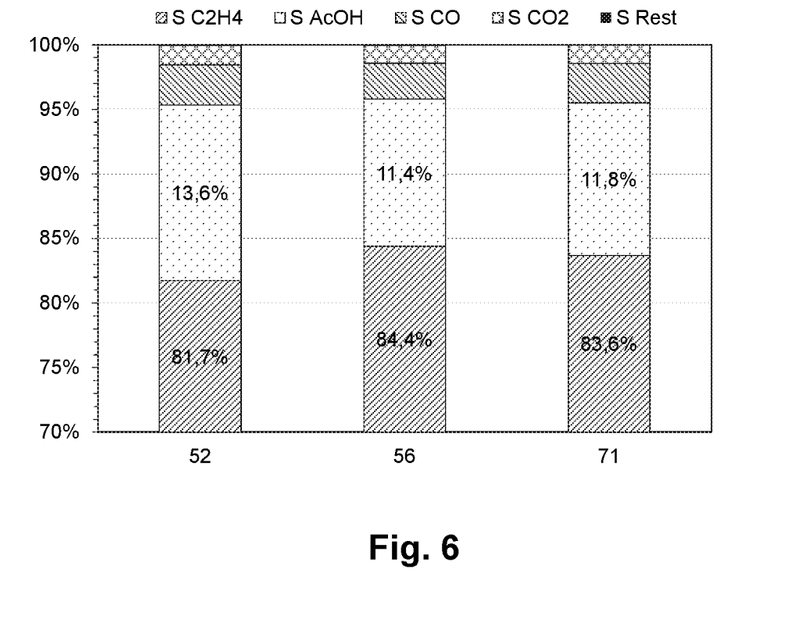
FIG. 6 shows experimental data according to an embodiment of the invention.

FIG. 6 shows the results of three selected experiments 52, 56 and 71 which were performed in the course of a comprehensive experimental series using a pilot reactor. In turn, in the context of the entire experimental series, a strong correlation between the product ratio of ethylene to acetic acid and the water partial pressure at the outlet of the reactor was observed. This applies to different conversions and different process conditions, i.e. altered compositions, flow rates, pressures and temperatures.

Experiments 52 and 71 were performed at identical space velocities of 0.9 kg of ethane/(kg of catalyst×h); in experiment 56, by contrast, said space velocity was 1.4 kg of ethane/(kg of catalyst×h). The water partial pressures at the reactor inlet were 0.56 bar for experiment 52, 0.58 bar for experiment 56 and 0.46 bar for experiment 71. In other words in experiments 52 and 56 virtually identical water partial pressures at the reactor inlet were used and for experiment 71 the water partial pressure at the reactor inlet differed markedly. The water partial pressures at the reactor outlet were 1.28 bar for experiment 52, 0.99 bar for experiment 56 and 1.00 bar for experiment 71. In other words in experiments 56 and 71 virtually identical water partial pressures at the reactor outlet were observed and for experiment 52 the water partial pressure at the reactor outlet differed markedly. The different water partial pressures at the reactor outlet between experiments 52 and 56 resulted from the different space velocities at substantially identical water partial pressures at the reactor inlet.

The experimental conditions for the experiments 52, 56 and 71 are summarized again in the table which follows. The salt temperature represents here the temperature of a salt melt used for cooling the reactor and therefore forms a measure for the reactor temperature:

|  | Experiment No. | | |
| --- | --- | --- | --- |
|  | 52 | 56 | 71 |
| Reactor inlet pressure [bar (abs.)] | 3.81 | 3.67 | 3.10 |
| Space velocity [kg of ethane/(kg of catalyst × h)] | 0.9 | 1.4 | 0.9 |
| Water/ethane [mol/mol] |  | 0.26 |  |
| Oxygen/ethane [mol/mol] | 0.35 | 0.31 | 0.33 |
| Salt temperature [° C.] | 302 | 316 | 311 |

-continued

|  | Experiment No. | | |
| --- | --- | --- | --- |
|  | 52 | 56 | 71 |
| Water partial pressure at reactor inlet [bar (abs.)] | 0.56 | 0.58 | 0.46 |
| Water partial pressure at reactor outlet [bar (abs.)] | 1.28 | 0.99 | 1.00 |

Experiment 52 employed an input comprising 56.7 mol percent of ethane, 19.6 mol percent of oxygen, 14.8 mol percent of water and 8.9 mol percent of nitrogen, experiment 56 an input comprising 60.2 mol percent of ethane, 18.4 mol percent of oxygen, 15.8 mol percent of water and 5.7 mol percent of nitrogen and experiment 71 an input comprising 57.3 mol percent of ethane, 18.8 mol percent of oxygen, 14.9 mol percent of water and 9.0 mol percent of nitrogen.

FIG. 6 shows values for the selectivity (S) for ethylene (C2H4), acetic acid (AcOH), carbon monoxide (CO), Carbon dioxide (CO2) and residual compounds (remainder, not visible due to low values) for the three experiments 52, 56 and 71. The ordinate shows the values concerning the selectivities. Ethane conversion differed by no more than 5% in all three experiments 52, 56 and 71.

It is clearly apparent that for the experiments 56 and 71 similar product ratios are observable at similar water partial pressures at the outlet at different water partial pressures at the inlet. The ratio of the product molar flows of acetic acid to ethylene (which here corresponds to the ratio of the corresponding selectivities) is about 0.14 in each of experiments 56 and 71. By contrast, in the experiments 52 and 56 similar water partial pressures are present at the inlet but on account of the altered space velocities markedly different water partial pressures are present at the outlet. Despite similar water partial pressures at the inlet, markedly different product ratios also result for the experimental points 52 and 56. The ratio of the product molar flows of acetic acid to ethylene is about 0.17 for experiment 52 and is thus above the value for experiment 56 mentioned above.

The invention claimed is:

1. Process for producing ethylene and acetic acid in which an ethane- and oxygen-containing reaction input stream is formed and a portion of the ethane and of the oxygen in the reaction input stream is converted into the ethylene and the acetic acid by oxidative dehydrogenation using a catalyst containing at least the elements molybdenum, vanadium, niobium and optionally tellurium to obtain a process gas, wherein the process gas contains the unconverted portion of the ethane and of the oxygen, the ethylene and the acetic acid and also water, wherein the process comprises adjusting a water partial pressure of the process gas according to a specified product ratio of the acetic acid to the ethylene to a value in a range between 0.5 and 5 bar (abs.), wherein one or more reactors are used for the oxidative dehydrogenation and the water partial pressure of the process gas is measured at a reactor outlet of the reactor(s) and wherein at least one of an addition of water to the reaction input stream and an adjustment of a reactor temperature is performed on the basis of said measuring the water partial pressure of the process gas at said reactor outlet of the reactor(s).

2. Process according to claim 1 in which the water partial pressure in the process gas is adjusted in a range between 0.7 and 3 bar (abs.).

3. Process according to claim 1 in which the ethane conversion in the oxidative dehydrogenation is greater than 15%.

4. Process according to claim 1 in which the reactor(s) comprise at least one catalyst bed, wherein the oxidative dehydrogenation is performed at a temperature range from 240° C. to 500° C. in the reactor bed(s) of the reactor(s).

5. Process according to claim 1 in which the reactor(s) comprise at least one catalyst bed, wherein a space velocity in the catalyst bed(s) of the reactor(s) is in a range between 0.1 and 10 kg of ethane/(h×kg of catalyst).

6. Process according to claim 1 in which a total pressure at a reactor inlet of the reactor(s) is between 1 and 10 bar (abs.).

7. Process according to claim 1 in which one or more diluents that pass into the process gas are further added to the reaction input stream.

8. Process according to claim 7 in which the diluent(s) is or are selected from the group consisting of water, methane, nitrogen, carbon dioxide, at least one inert gas, and mixtures thereof.

9. Process according to claim 1 in which ethylene is further added to the reaction input stream.

10. Process according to claim 1 in which an input mixture containing ethylene and ethane is added to the reaction input stream.

* * * * *